US010150986B2

(12) United States Patent
Brennan et al.

(10) Patent No.: US 10,150,986 B2
(45) Date of Patent: Dec. 11, 2018

(54) BIOSENSORS COMPRISING CONCATEMERIC NUCLEIC ACID MOLECULES

(71) Applicant: McMaster University, Hamilton (CA)

(72) Inventors: John D. Brennan, Dundas (CA); Yingfu Li, Dundas (CA); Carmen Carrasquilla, Hamilton (CA)

(73) Assignee: MCMASTER UNIVERSITY, Hamilton (CA)

( * ) Notice: Subject to any disclaimer, the term of this patent is extended or adjusted under 35 U.S.C. 154(b) by 0 days.

(21) Appl. No.: 15/079,418

(22) Filed: Mar. 24, 2016

(65) Prior Publication Data

US 2016/0281145 A1    Sep. 29, 2016

Related U.S. Application Data

(60) Provisional application No. 62/137,312, filed on Mar. 24, 2015.

(51) Int. Cl.
| | |
|---|---|
| *C12Q 1/68* | (2018.01) |
| *C12Q 1/6818* | (2018.01) |
| *C12Q 1/6825* | (2018.01) |
| *C12Q 1/6834* | (2018.01) |
| *G01N 33/53* | (2006.01) |
| *C12Q 1/6816* | (2018.01) |

(52) U.S. Cl.
CPC ......... *C12Q 1/6818* (2013.01); *C12Q 1/6816* (2013.01); *C12Q 1/6825* (2013.01); *C12Q 1/6834* (2013.01); *G01N 33/5308* (2013.01)

(58) Field of Classification Search
None
See application file for complete search history.

(56) References Cited

U.S. PATENT DOCUMENTS

| | | | |
|---|---|---|---|
| 5,854,033 A | 12/1998 | Lizardi | |
| 6,210,884 B1 | 4/2001 | Lizardi | |
| 2005/0089864 A1 | 4/2005 | Li | |
| 2012/0252699 A1* | 10/2012 | Jaffrey | A61K 49/0032 506/16 |

OTHER PUBLICATIONS

Su et al(Langmuir, 2007, 23 (3), pp. 1300-1302).*
Pelton et al. (Biomacromolecules 2008, 9, 935-941) and.*
C. Carrasquilla, J.R.L. Little, Y. Li, J.D. Brennan. Developing Concatemeric Structure-Switching Signaling DNA Aptamers using Rolling Circle Amplification. 96th Canadian Chemistry Conference and Exhibition. May 29, 2013.
C. Carrasquilla, et al. "Patterned paper sensors printed with long-chain DNA aptamers". Chem. Eur. J., 2015, 21(20):7369-7373.
C. Carrasquilla, et al.,"Patterned Paper Sensors Printed with Concatemeric DNA Aptamers". 98th Canadian Chemistry Conference and Exhibition. Jun. 14, 2015.

* cited by examiner

*Primary Examiner* — Kimberly Chong
(74) *Attorney, Agent, or Firm* — Bereskin & Parr LLP/S.E.N.C.R.L., s.r.l.; Patricia Folkins

(57) ABSTRACT

The present application relates to biosensors, for example comprising an high-molecular weight, tandem repeating, structure-switching nucleic acid aptamers (concatemeric aptamers) to rapidly create patterned sensors via, for example, inkjet printing. These concatemeric aptamer reporters remain immobilized at the point of printing through strong adsorption but retain sufficient segmental mobility to undergo structure switching and reporter signalling to provide both qualitative and quantitative detection of one or more analytes. In certain embodiments, inkjet printing allows for the patterning of internally referenced sensors with multiplexed detection, and provides a generic platform for on-demand printing of sensors even in remote locations.

12 Claims, 14 Drawing Sheets

Specification includes a Sequence Listing.

a) After lateral flow with buffer

Concatemer/FDNA  Concatemer/FDNA/QDNA b) After target addition 1  0  0.05 0.08 0.1 0.25 0.5  1  2  3
ATP (mM)

BIOSENSORS COMPRISING CONCATEMERIC NUCLEIC ACID MOLECULES

The present application claims the benefit of provisional patent application No. 62/137,312, filed Mar. 24, 2015, the contents of which are herein incorporated by reference.

INCORPORATION OF SEQUENCE LISTING

A computer readable form of the Sequence Listing "3244-P48209US01_SequenceListing.txt" (4,096 bytes), submitted via EFS-WEB and created on Mar. 25, 2016 and amended on Apr. 6, 2017, is herein incorporated by reference.

FIELD

The present application relates to biosensors comprising one or more concatemeric nucleic acid molecules and at least one reporter molecule which are absorbed on a substrate using non-chemical means.

BACKGROUND

Due to its portability, abundance and low cost, paper has drawn increasing interest as a platform for sensing devices, particularly in the field of point-of-care (POC) diagnostics and disease screening applications for the developing world.[1] Currently, the main techniques to fabricate paper-based biosensors involve either conjugating the biological sensing elements to the paper surface by chemical modification of the paper fibers,[2] entrapping these biomolecules within sol-gel derived inks,[3] or localizing adsorbed biomolecules using hydrophobic barriers to define channels created by photolithography, etching, plasma treatment, flexographic or screen printing methods.[4] However, such approaches can be laborious, prone to non-specific binding, and may require many complex reactions, which can make fabrication inconvenient and increase cost.

DNA aptamers have become important sensing elements due to their thermal and chemical stability, versatility in target recognition (from small molecules to whole cells), high affinity and specificity, and ease of synthesis and manipulation[5]—all inherent advantages over conventional antibody and enzyme-based sensors.[6] However, aptamers have rarely been explored for paper-based diagnostics since they suffer from some of the same issues as proteins in their need for complex immobilization strategies or conjugation to species such as nanoparticles or microbeads for localization on paper.[7]

Extremely long, tandem repeating DNA molecules can easily be produced by a biochemical technique known as rolling circle amplification (RCA)—an isothermal process in which a special DNA polymerase, such as φ29 DNA polymerase, extends a short DNA primer by making round-by-round copies of a circular DNA template[8]—and have been extensively explored for bioanalytical applications to detect a variety of targets,[9] and for various nanotechnology applications.[10]

SUMMARY

Rolling circle amplification (RCA) products containing tandem repeating structure-switching (reporter) nucleic acid aptamers (referred to as long-chain or concatemeric aptamers) deposited, for example by inkjet printing, as patterns directly onto, for example, unmodified paper surfaces have been developed and shown to remain immobilized at their initial deposited locations after flow of liquids over the sensing area, and retain sufficient local and segmental motion required for structure-switching and signaling to occur after introduction of target analytes.

Accordingly, the present application includes a biosensor for detecting an analyte comprising:
  a) a substrate; and
  b) one or more reporter layers absorbed on the substrate, each of the one or more reporter layers comprising one or more concatemeric nucleic acid molecules and one or more reporter nucleic acid molecules for detection of the analyte,
wherein the one or more reporter layers are absorbed on the substrate by non-chemical means selected from printing and spotting.

The present application also includes assay methods that utilize the biosensor of the present application. In an embodiment, the assay is a method of detecting one or more analytes in a sample, wherein the sample is suspected of comprising the one or more analytes, the method comprising contacting the sample with the biosensor of the application and monitoring the one or more reporter nucleic acid molecules for detection for a positive or negative result, wherein a positive result indicates the presence of the one or more analytes in the sample.

The present application further includes kits comprising the biosensors of the application. In an embodiment, the kit includes the biosensor and any further reagents for performing an assay using the biosensor. In a further embodiment, the kit includes instructions for using the biosensor in the assay and any controls needed to perform the assay. The controls may be on the biosensor itself, or alternatively, on a separate substrate. In a further embodiment, the kit includes all the components required to perform any of the assay methods of the present application.

The present application also includes a method for preparing a biosensor of the application comprising:
  a) subjecting a circular nucleic acid template that is specific for an analyte to rolling circle amplification (RCA) to provide concatemeric nucleic acid molecules;
  b) combining the concatemeric nucleic acid molecules with one or more reporter nucleic acid molecules, each comprising a sequence that is complimentary to a portion of the concatemeric nucleic acid molecule, wherein the combining is under conditions for the hybridization of the one or more reporter nucleic acid molecules to the concatemeric nucleic acid molecule to provide reporter nucleic acid aptamers; and
  c) depositing the structure-switching nucleic acid aptamers onto a substrate by non-chemical means selected from printing and spotting.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which.

Figure 3:
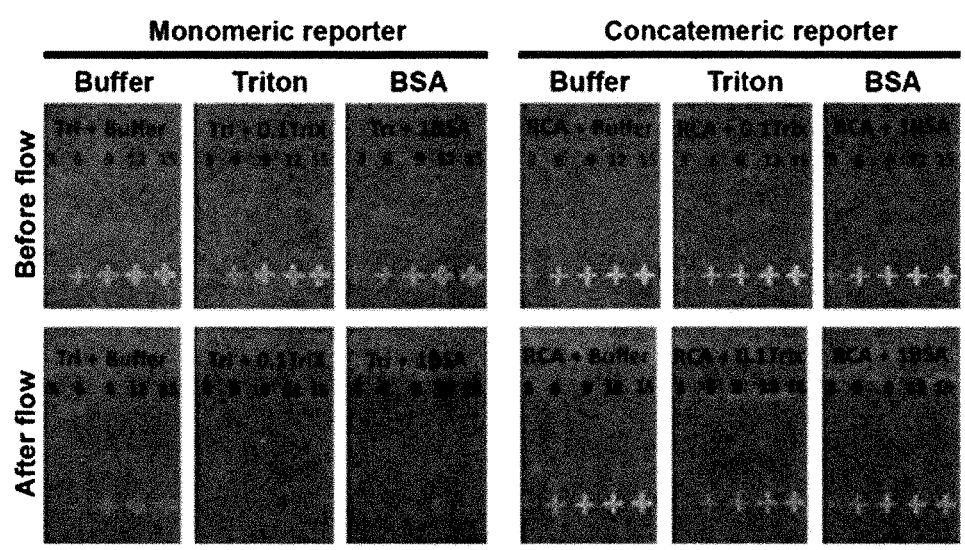

FIG. 3 shows fluorescence images of exemplary paper sensors before and after lateral flow in pure buffer, buffer with 0.1% Triton-X, or buffer with 1% BSA. Each paper device was inkjet-printed with 3-15 layers of either monomeric or concatemeric ATP aptamer reporter ("+") and cyan toner for labels (dark letters).

Figure 4:

FIG. 4 shows fluorescence images of the concatemeric and monomeric ATP aptamers before and after the addition of buffer or ATP in exemplary embodiments of the application.

Figure 5:
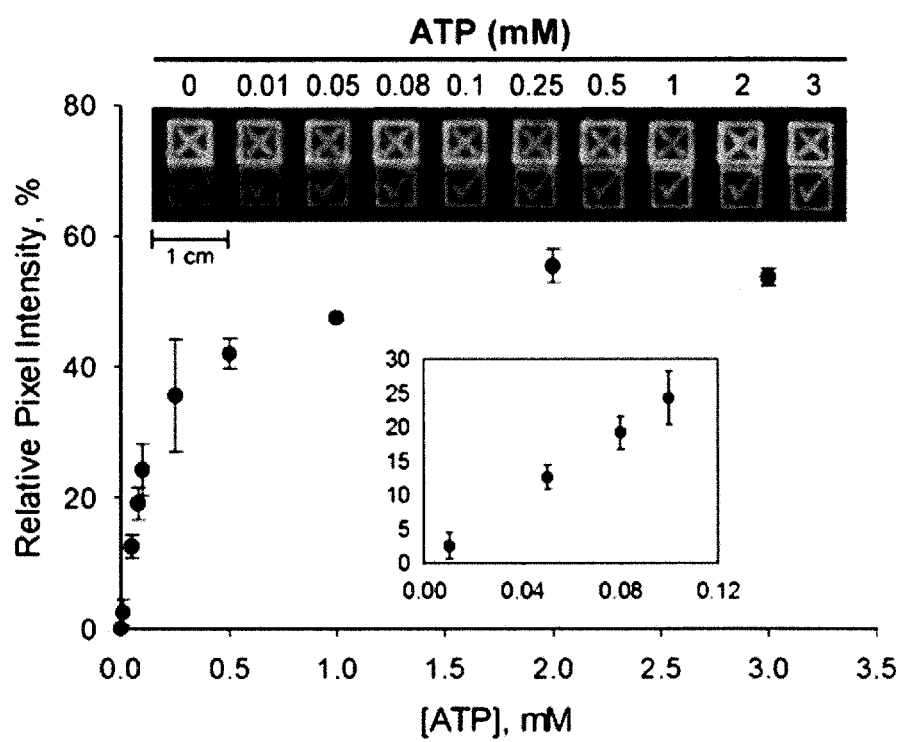

FIG. 5 shows response of the exemplary concatemeric reporter with increasing concentrations of ATP, wherein ☑ represents aptamer/FDNA/QDNA and ☒ represents aptamer/FDNA.

Figure 6:
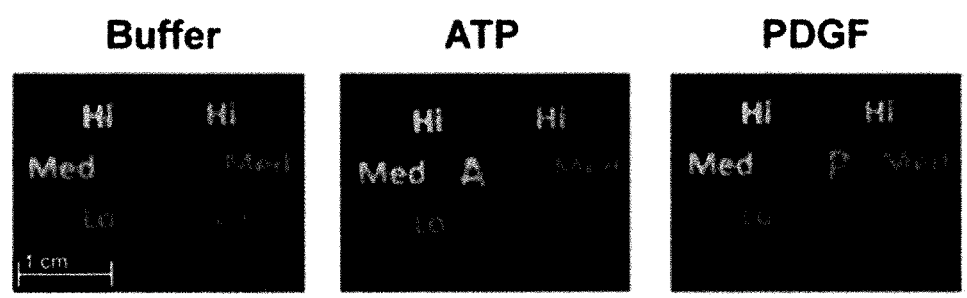

FIG. 6 shows fluorescence response of binary letter exemplary sensors treated with buffer, 2 mM ATP or 200 nM PDGF (A: ATP and P: PDGF concatemeric reporters—aptamer/FDNA/QDNA). Signal intensity references ("0", "Lo", "Med", "Hi") consist of increasing print layers of concatemeric ATP aptamer/FDNA.

Figure 7:
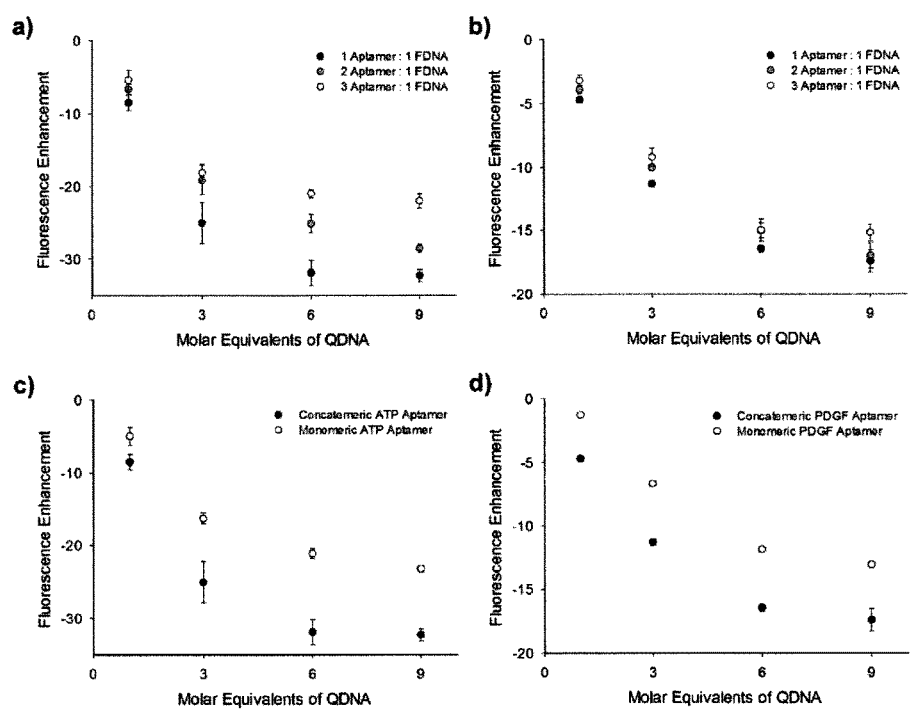

FIG. 7 shows optimization of aptamer reporter quenching using various QDNA molar equivalents in exemplary embodiments of the application. Fluorescence quenching of the concatemeric a) ATP aptamer and b) PDGF aptamer with increasing molar equivalents of both the aptamer unit and QDNA to FDNA. Fluorescence quenching of the c) ATP-binding and d) PDGF-binding concatemeric or monomeric aptamers pre-incubated with FDNA in a 1:1 ratio upon addition of increasing molar equivalents of QDNA.

Figure 8:
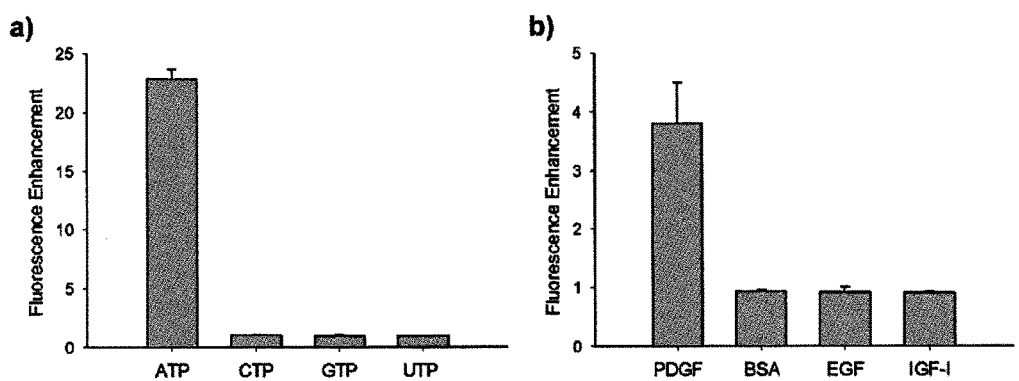

FIG. 8 shows selectivity of exemplary concatemeric DNA aptamers in solution. Selectivity of the a) concatemeric ATP aptamer to different nucleotides at 1 mM and b) concatemeric PDGF aptamer to different growth factors and proteins at 100 nM.

Figure 9:
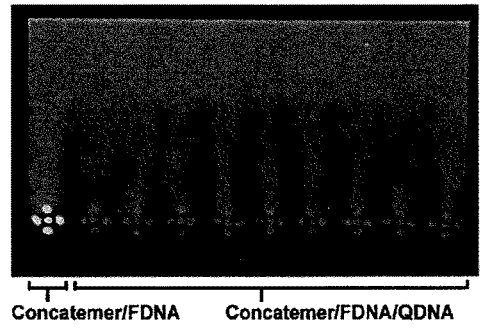
Figure 9:
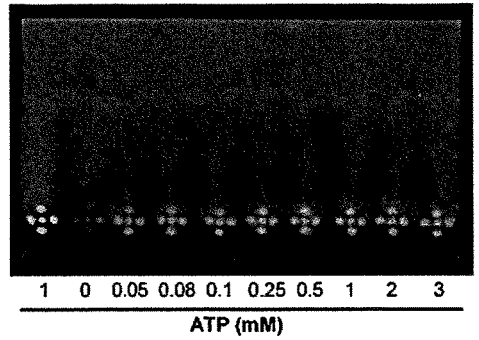

FIG. 9 shows manual deposition assay of concatemeric DNA aptamers on paper in an exemplary embodiment of the application. Fluorescence image of the concatemeric ATP aptamer following manual pipette deposition and a) lateral flow with buffer, then b) addition of increasing concentrations of ATP.

Figure 10:
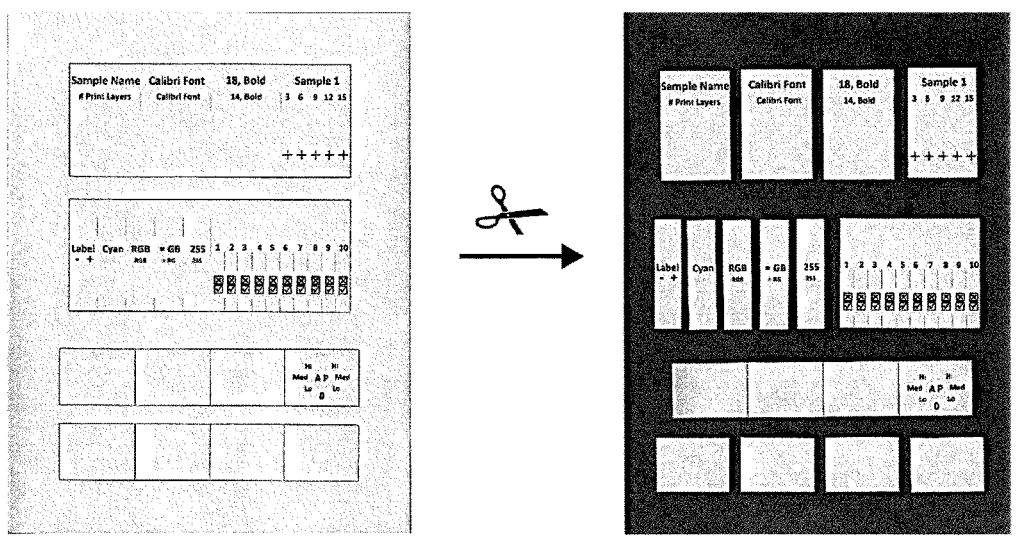

FIG. 10 shows an exemplary paper printing sample. Example paper with printed lines and labels for sensor fabrication before and after cutting to sensor size.

Figure 11:
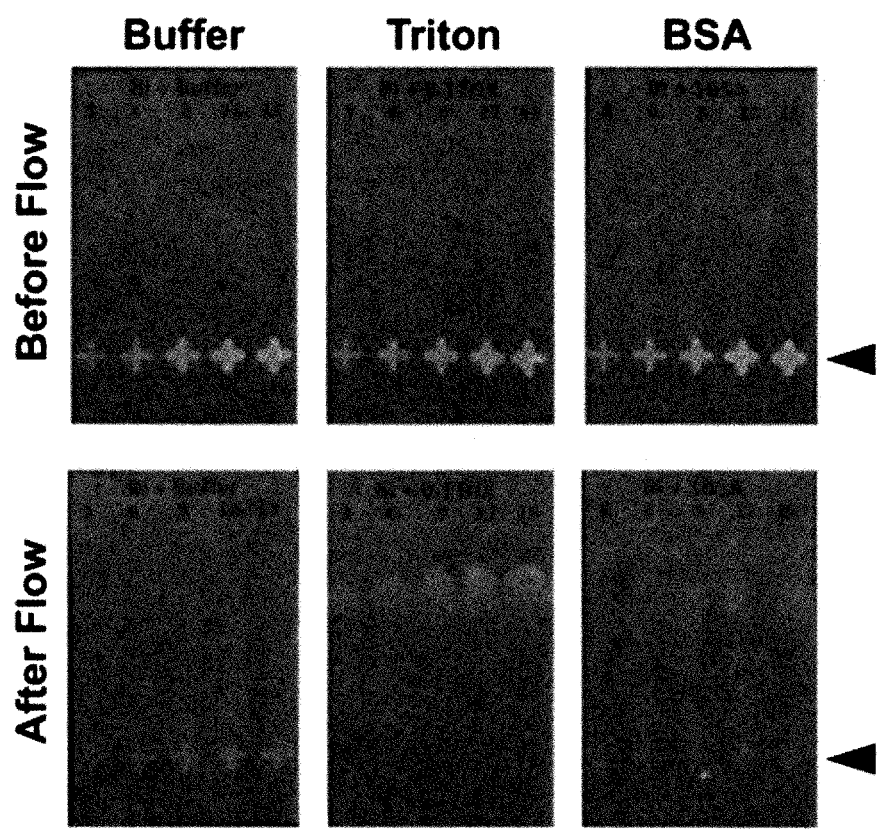

FIG. 11 shows fluorescent images of exemplary paper devices before and after lateral flow. Each paper device was printed with 3, 6, 9, 12, or 15 layers of the monomeric bipartite ATP aptamer reporter. Lateral flow was done in pure buffer, buffer containing 0.1% Triton-X 100, and buffer with 1% BSA. Arrows indicate where aptamers were printed.

Figure 12:
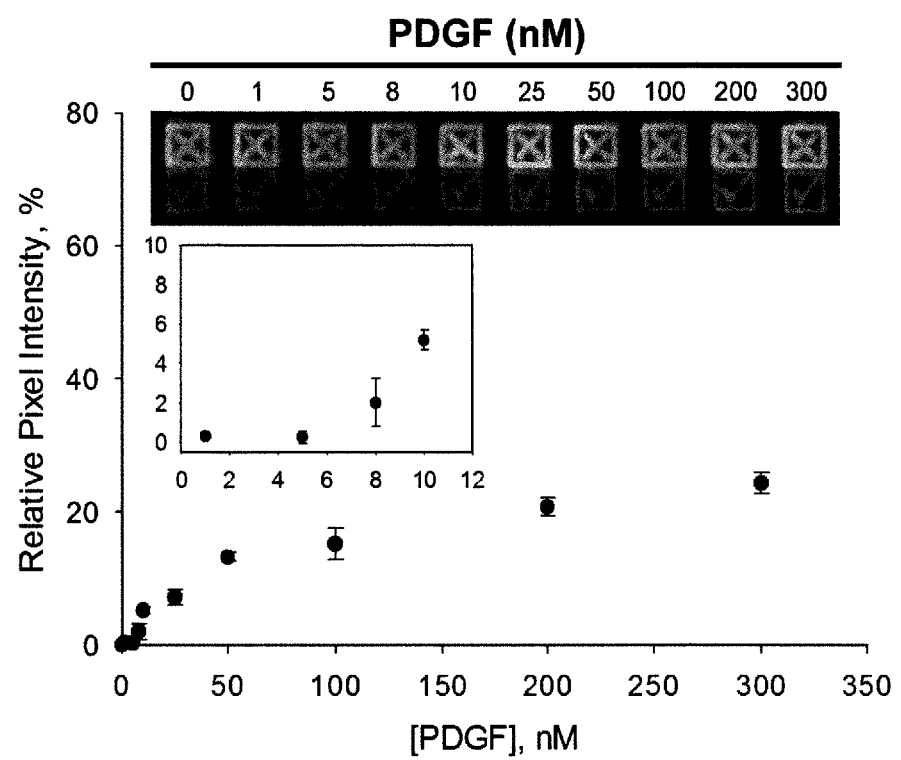

FIG. 12 shows signal response of the exemplary concatemeric PDGF aptamer reporter with increasing concentrations of PDGF-BB. Inset shows representative image of the target concentration-dependent curve, wherein ☑ represents aptamer/FDNA/QDNA and ☒ represents aptamer/FDNA.

Figure 13:
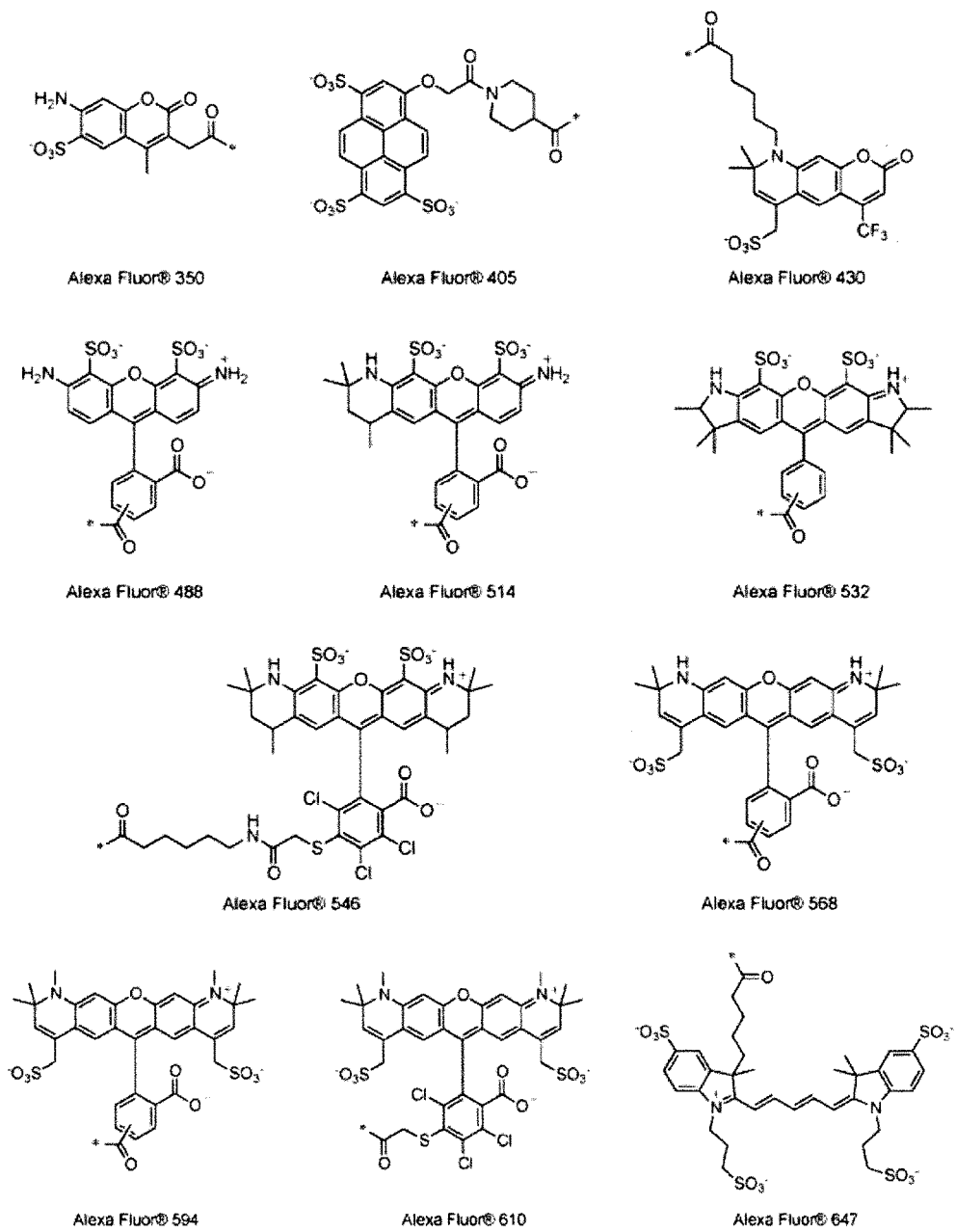

FIG. 13 shows the structures of some of the known Alexa Fluor™ dyes. The "*" indicates the point of attachment of the dye to the reporter nucleic acid molecule.

Figure 14:
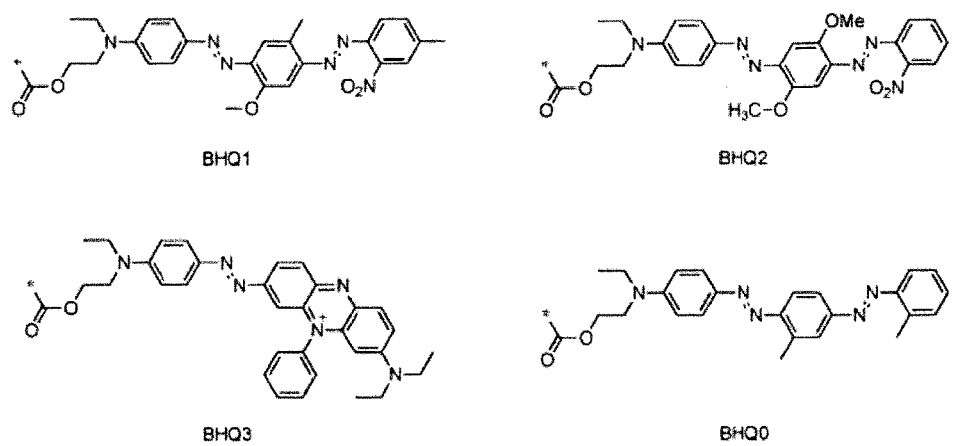

FIG. 14 shows the structures of some known blackhole quenchers (BHQs).

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

The term "substrate" as used herein refers to any solid support to which one or more concatemeric nucleic acid molecules can be printed or spotted.

The term "paper" or "paper-based material" as used herein refers to a commodity of thin material produced by the amalgamation of fibers, typically plant fibers composed of cellulose, which are subsequently held together by hydrogen bonding.

As used herein, the term "immobilized" or synonyms thereof in reference to the one or more concatemeric nucleic acid molecules, means that the movement of the one or more concatemeric nucleic acid molecules of the biosensor is restricted.

The term "analyte" as used herein means any agent, including, but not limited to, small inorganic and organic molecules, metal ions, hormonal growth factors, biomolecules, toxins, biopolymers (such as carbohydrates, lipids, peptides and proteins), cells, tissues and microorganisms (including bacteria and viruses), for which one would like to sense or detect using a biosensor of the present application. In an embodiment, the analyte is either isolated from a natural source or is synthetic. The term analyte also includes mixtures of compounds or agents such as, but not limited to, combinatorial libraries and samples from an organism or a natural environment.

The term "sample(s)" as used herein refers to any material that one wishes to assay using the biosensor of the application. The sample may be from any source, for example, any biological (for example human or animal medical samples), environmental (for example water or soil) or natural (for example plants) source, or from any manufactured or synthetic source (for example food or drinks). The sample is one that comprises or is suspected of comprising one or more analytes.

The term "one or more reporter nucleic acid molecules for detection" as used herein refers to one or more nucleic acid molecules that comprise molecules that are used to detect the presence of analyte. Detection is performed using any available method, including, for example, colorimetric, electrochemical and/or spectroscopic methods.

The term "nucleic acid" refers to polynucleotides such as deoxyribonucleic acid (DNA) and ribonucleic acid (RNA).

The term "aptamer" as used herein refers to short, chemically synthesized, single stranded (ss) RNA or DNA oligonucleotides which fold into specific three-dimensional (3D) structures that bind to a specific analyte with dissociation constants, for example, in the pico- to nano-molar range.

The term "structure-switching nucleic acid aptamers" or "reporter nucleic acid aptamers" as used herein refers to aptamer-based reporters that function by switching structures from a DNA/DNA or RNA/RNA complex to a DNA/analyte or RNA/analyte complex.

The term "concatemeric nucleic acid molecules" or "concatemer" as used herein refers to a long continuous DNA or RNA molecule that contains multiple copies of the same DNA or RNA sequences linked in a tandem series.

The term "rolling circle amplification" as used herein refers to a unidirectional nucleic acid replication that can rapidly synthesize multiple copies of circular molecules of DNA or RNA. In an embodiment, rolling circle amplification is an isothermal enzymatic process where a short DNA or RNA primer is amplified to form a long single stranded DNA or RNA using a circular DNA template and an appropriate DNA or RNA polymerase. The product of this process is a concatemer containing ten to thousands of tandem repeats that are complimentary to the circular template.

The term "non-chemical" as used herein refers absorption means (i.e. for absorbing the concatemeric nucleic acid molecules to the substrate) other than those that require a chemical bond between the concatemeric nucleic acid molecule and the substrate.

The term "spotting" as used herein refers to the placement of a substance, such as the concatemeric nucleic acid molecules, on a substrate using a device that manually drops the substance onto the substrate, such as a tube, pipette or a capillary.

The term "printing" as used herein refers to the placement of a substance, such as the concatemeric nucleic acid molecules, on a substrate using a mechanical device that prints the substance onto the substrate.

The term "detection system" as used herein refers to a combination of molecules that interact together to provide a signal that is detected.

As used in this specification and the appended claims, the singular forms "a", "an" and "the" include plural references unless the content clearly dictates otherwise. Thus for example, a composition containing "an analyte" includes one such analyte or a mixture of two or more analytes.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific synthetic manipulation to be performed, and the identity of the molecule(s) to be transformed, but the selection would be well within the skill of a person trained in the art. All process/method steps described herein are to be conducted under conditions sufficient to provide the product shown. A person skilled in the art would understand that all reaction conditions, including, for example, reaction solvent, reaction time, reaction temperature, reaction pressure, reactant ratio and whether or not the reaction should be performed under an anhydrous or inert atmosphere, can be varied to optimize the yield of the desired product and it is within their skill to do so.

II. Biosensors of the Application

The biosensors reported herein are prepared by printing or spotting one or more concatemeric nucleic acid molecules onto substrates, such as paper-based substrates. In some embodiments, inkjet printing methods, such as thermal inkjet printing, were used to print layers of one or more concatemeric nucleic molecules as reporter layers on the substrate. The location and pattern of the one or more printed or spotted concatemeric nucleic acid molecules depended on the specific arrangements required for the assay. In an embodiment, the assays were based on lateral flow of a sample solution up the substrate by capillary action, passing through the one or more reporting layers, wherein the solution comprised, or was suspected of comprising, an analyte to be detected. In another embodiment, the assays were based on a method of spotting a sample, for example using a pipette for deposition of the sample solution on the substrate, wherein the sample was suspected of comprising one or more analytes to be detected.

Therefore, the present application includes a biosensor for detecting an analyte comprising:
  a) a substrate; and
  b) one or more reporter layers absorbed on the substrate, each of the one of more reporter layers comprising one or more concatemeric nucleic acid molecules and one or more reporter nucleic acid molecules for detection of the analyte,
wherein the one or more reporter layers are absorbed on the substrate by non-chemical means selected from printing and spotting.

The present application also includes a biosensor for detection of an analyte comprising:
  a) a substrate having a first end and second end;
  b) one or more reporter layers absorbed on the substrate, each of the one or more reporter layers comprising one or more concatemeric nucleic acid molecules and one or more reporter nucleic acid molecules for detection of the analyte,
wherein immersion of the first end of the substrate in a solution comprising the analyte results in lateral flow of the solution from the first end of the substrate to the second end by capillary action and the flow passing through the one or more reporter layers resulting in binding of the analyte with the concatemeric nucleic acid molecules, the binding being detected by the one or more reporter nucleic acid molecules for detection of the analyte.

In an embodiment, the one or more concatemeric nucleic acid molecules comprise RNA aptamers or DNA aptamers, or a mixture thereof. In a further embodiment, the one or more concatemeric nucleic acid molecules comprise tandem repeating nucleic acid aptamers.

In an embodiment, the aptamers interact with and bind to their respective analytes through structural recognition. In an embodiment, the aptamers are produced using Systematic Evolution of Ligands by EXponential enrichment (SELEX) technology.

In an embodiment, the detection of the analyte is performed by monitoring for the presence of a product formed, for example, by the interaction of the one or more reporter nucleic acid molecules with the analyte. In this embodiment, the product being formed possesses a detectable signal (for e.g., fluorescence) that is distinct from the signal of any of the starting reagents.

In an embodiment, the one or more reporter nucleic acid molecules comprise a detection system. In an embodiment, the detection system is selected from a fluorescent system, a colorimetric system and an electrochemical system.

In a further embodiment, the one or more reporter nucleic acid molecules comprise a fluorescent system. In a further embodiment, the fluorescent system comprises a fluorescent molecule and a corresponding quencher molecule. In a further embodiment, the interaction of the reporter layer with an analyte results in the displacement of the corresponding quencher molecule, resulting in a distinct detectable fluorescent signal.

In an embodiment, the fluorescent system comprises a fluorophore and a corresponding quencher. In a further embodiment, the fluorophore is a chemical fluorophore selected from fluorescein, rhodamine, coumarin and cyanine, Alexa Fluor™ dyes (see for e.g. FIG. 13) and derivatives thereof. In an embodiment, the selection of the fluorophore for the biosensor is based upon one or more parameters including, but not limited to, (i) maximum excitation and emission wavelength, (ii) extinction coefficient, (iii) quantum yield, (iv) lifetime, (v) stokes shift, (vi) polarity of the fluorophore and (vii) size. In an embodiment, the fluorophore is fluorescein.

A quencher molecule is a substance with no native fluorescence and that absorbs the excitation energy from a fluorophore and dissipates the energy as heat, with no emission of fluorescence. Thus, when the fluorophore and quencher are close in proximity, the fluorophore's emission is suppressed. In an embodiment, the quencher molecule is selected from dimethylaminoazobenzenesulfonic acid (dabcyl) and fluorescence resonance energy transfer (FRET or blackhole) quenchers, such as those shown in FIG. 14, and derivatives thereof.

In an embodiment, the nucleic acid aptamers comprise a first nucleic acid sequence that is complimentary to a first reporter nucleic acid molecule and a second nucleic acid sequence that is complimentary to a second reporter nucleic acid molecule, wherein the first reporter nucleic acid molecule comprises a fluorescent molecule and the second reporter nucleic acid molecule comprises a corresponding quencher molecule for the fluorescent molecule and the first nucleic acid sequence and the second nucleic acid sequence are located on the nucleic acid aptamer at positions wherein the fluorescence of the fluorescent molecule is quenched by the quenching molecule in the absence of analyte.

In an embodiment, in the presence of analyte, the quenching molecule is displaced resulting in fluorescence.

In an embodiment, a complex is formed between an aptamer, a fluorophore-labelled nucleic acid molecule (first reporter nucleic acid molecule) and a quencher-molecule nucleic acid molecule (second reporter nucleic acid molecule). In an embodiment, this complex is a structure switching nucleic acid aptamer or a reporter nucleic acid aptamer. When the analyte is absent, the fluorophore-labelled nucleic acid molecule binds to the second reporter nucleic acid molecule comprising the corresponding quencher molecule, bringing the fluorescent molecule and the corresponding quencher molecule into close proximity for maximum fluorescence quenching. When the analyte is introduced, a switch of the binding partners for the fluorophore-labelled nucleic acid molecule occurs in which the reporter nucleic acid molecule comprising the quencher is replaced the analyte. The switch of binding partners is in conjunction with the generation of a strong fluorescence signal owing to the dissociation of the second reporter nucleic acid molecule comprising the corresponding quencher molecule.

In an embodiment, the nucleic acid aptamers retain local and segmental motion to bind an analyte upon absorption to the substrate. In another embodiment, the molecular weight of the concatemeric nucleic acid molecules is such that it prevents global motion and immobilizes the concatemeric nucleic acid molecules to the substrate. In an embodiment, the concatemeric nucleic acid molecules are comprised of tens to thousands of nucleic acid aptamers. In a further embodiment, concatemers are produced through rolling circle amplification (RCA).

The immobilization of the reporter layer is in part affected by the size of the concatemeric nucleic acid molecules. Accordingly, it is an embodiment that the concatemeric nucleic acid molecules comprise high-molecular-weight nucleic acid aptamers. In an embodiment, the preparation high-molecular-weight concatemeric nucleic acid molecules comprise at least 400 nucleotides and hundreds to thousands of aptamer repeats in tandem. In a further embodiment, the concatemeric nucleic acid molecules have a molecular weight of from about 10,000 to 1,000,000,000 Da.

In an embodiment, the reporter layer remains immobilized at its initial absorbed locations on the substrate. In a further embodiment, the reporter layer remains immobilized at its initial locations after flow of the analyte solution over the reporter layer.

Immobilization is accomplished by the large molecular weight of the concatemeric nucleic acid molecules. In a further embodiment, the large molecular weight of the concatemeric nucleic acid molecules promote further immobilization by physical means such as electrostatic interactions, hydrogen-bonding, bioaffinity or combinations thereof.

In an embodiment, the concatemeric nucleic acid molecules are produced by rolling circle amplification (RCA).

In an embodiment, the substrate comprises a substantially planar surface, and is made of material that supports lateral flow of a solution. When the solution is aqueous based, the substrate is hydrophilic in nature. For aqueous solutions, therefore, the substrate may be made from, for example, a paper based material. In further embodiments, the substrate is made from paper, glass, plastic, polymers, metals, ceramics, alloys or composites. In another embodiment, the substrate is made from paper or paper-based material. In still other embodiments, the substrate is in the shape of a rectangular strip, with the first and second ends being opposed to each other. In a further embodiment, the substrate is a rectangular test strip.

In an embodiment, the "paper" or "paper-based material" is an amalgamation of plant fibers composed of cellulose. In an embodiment, the plant fibers are from wood pulp from pulpwood trees. In an embodiment, the plant fibers are from pulpwood, cotton, hemp, linen and rice, or a mixture thereof. While the fibers used are usually natural in origin, it is an embodiment that a wide variety of synthetic fibers, such as polypropylene and polyethylene, are incorporated into the paper as a way of imparting desirable physical properties. In embodiments, the paper is hydrophilic or hydrophobic, has a surface coating and/or incorporates fillers that provide desirable physical properties prior to coating with the inkjet deposited or spotting of the one or more concatemeric nucleic acid molecules.

In an embodiment, the reporter layer is comprised of multiple layers of the concatemeric nucleic acid molecules and one or more molecules for detection on the substrate. In a further embodiment, the reporter layer is comprised of about 1 to about 100 layers, about 5 to about 20 layers, or about 10 to about 15 layers, of the concatemeric nucleic acid molecules and one or more molecules for detection.

In an embodiment, more than one reporter layer is printed on a substrate. In a further embodiment, negative control layers and/or positive control layers are also printed on the same substrate. In a further embodiment, the substrate further comprises markings, printed using regular ink from a separate cartridge, that, for example, label each layer and/or delineate each layer. In a further embodiment, the reporter layers are printed in a specific pattern, for example, in the shape of a plus sign to indicate a positive result. In this example a corresponding negative control is optionally printed in the shape of a minus sign to indicate a negative result.

The versatility offered by combining the control of specific deposition of aptamer bioinks from printing and the direct immobilization of one or more reporter layers on a substrate is applied to multiplexing assays. This allows for simultaneous measurements of one or more analytes in a single run/cycle of the assay. Accordingly it is an embodiment that two or more different reporter layers, each comprising different concatemeric nucleic acids and reporter molecules for different analytes, are printed on the substrate.

III. Methods of the Application

The present application also includes a method for preparing the biosensor of the application, comprising:
a) subjecting a circular nucleic acid template that is specific for an analyte to rolling circle amplification (RCA) to provide concatemeric nucleic acid molecules;
b) combining the concatemeric nucleic acid molecules with one or more reporter nucleic acid molecules, each comprising a sequence that is complimentary to a portion of the concatemeric nucleic acid molecule, wherein the combining is under conditions for the hybridization of the one or more reporter nucleic acid molecules to the concatemeric nucleic acid molecule to provide reporter nucleic acid aptamers; and
c) depositing the reporter nucleic acid aptamers as a reporter layer onto a substrate by non-chemical means selected from printing and spotting.

In an embodiment, the concatemeric nucleic acid molecules comprise RNA aptamers or DNA aptamers, or a mixture thereof.

In an embodiment, the one or more reporter nucleic acid molecules form a detection system. In an embodiment, the detection system is selected from a fluorescent system, a colorimetric system and an electrochemical system.

In a further embodiment, the one or more reporter nucleic acid molecules form a fluorescent system. In a further embodiment, the fluorescent system comprises a fluorescent molecule and a corresponding quencher molecule.

In an embodiment, the fluorescent system comprises a fluorophore and a corresponding quencher. In a further embodiment, the fluorophore is a chemical fluorophore selected from fluorescein, rhodamine, coumarin and cyanine, Alexa Fluor™ (see for example, FIG. 13) and derivatives thereof. In an embodiment, the selection of the fluorophore for the biosensor is based upon one or more parameters including, but not limited to, (i) maximum excitation and emission wavelength, (ii) extinction coefficient, (iii) quantum yield, (iv) lifetime, (v) stokes shift, (vi) polarity of the fluorophore and (vii) size. In an embodiment, the fluorophore is fluorescein.

A quencher molecule is a substance with no native fluorescence and that absorbs the excitation energy from a fluorophore and dissipates the energy as heat, with no emission of fluorescence. Thus, when the fluorophore and quencher are close in proximity, the fluorophore's emission is suppressed. In an embodiment, the quencher molecule is selected from dimethylaminoazobenzenesulfonic acid (dabcyl) and fluorescence resonance energy transfer (FRET or blackhole) quenchers, such as those shown in FIG. 14, and derivatives thereof.

In an embodiment, the concatemeric nucleic acid molecules are combined with (i) a first reporter nucleic acid molecule comprising a fluorescent molecule and a sequence that is complimentary to at least a first portion of the concatemeric nucleic acid molecule, and (ii) a second reporter nucleic acid molecule comprising a corresponding quencher molecule for the fluorescent molecule and a sequence that is complimentary to at least a second portion of the concatemeric nucleic acid molecule, wherein the first portion of the concatemeric nucleic acid molecule and the second portion of the nucleic acid molecule are located at positions for the fluorescence of the fluorescent molecule to be quenched by the quencher molecule when the first and second reporter molecules are hybridized to the concatemeric nucleic acid molecule and the combining is under conditions for the hybridization of the first reporter nucleic acid molecule and the second reporter nucleic acid molecule to the concatemeric nucleic acid molecule to provide a reporter nucleic acid aptamers.

In an embodiment, in the presence of analyte, the quenching molecule is displaced resulting in fluorescence from the fluorescent molecule.

In an embodiment, the reporter nucleic acid aptamers retain local and segmental motion to bind an analyte upon absorption to the substrate. In an embodiment, the molecular weight of the concatemeric nucleic acid molecules prevents global motion and immobilizes the concatemeric nucleic acid molecules to the substrate. In an embodiment, the concatemeric nucleic acid molecules have a molecular weight of from about 10,000 to 1,000,000,000 Da. In a further embodiment, the concatemeric nucleic acid molecules remain immobilized at their initial absorbed locations on the substrate.

To create the fluorescent reporter system of the biosensor, it is an embodiment that the molar ratios of the first reporter nucleic acid molecule and the second reporter nucleic acid molecule to bind the structure-switching nucleic acid aptamers are optimized to construct a pre-quenched complex. In an embodiment, the molar ratios are selected to ensure that the majority of the first reporter nucleic acid molecule comprising a fluorescent molecule anneals to the nucleic acid aptamer and also engage the second reporter nucleic acid sequence comprising a corresponding quencher molecule for the fluorescent molecule, for proper quenching and low background signal levels prior to target binding. In an embodiment, the molar ratio of the nucleic acid aptamer/first reporter nucleic acid molecule/second reporter nucleic acid molecule is in the range of about 1:1:1 to about 1:1:100. In a further embodiment, the molar ratio of the nucleic acid aptamer/first reporter nucleic acid molecule/second reporter nucleic acid molecule is about 1:1:50, about 1:1:25 or about 1:1:6.

In an embodiment, the substrate comprises a substantially planar surface, and is made of material that supports lateral flow of a solution. When the solution is aqueous based, the substrate is hydrophilic in nature. For aqueous solutions, therefore, the substrate may be made from, for example, a paper based material. In further embodiments, the substrate is made from paper, glass, plastic, polymers, metals, ceramics, alloys or composites. In another embodiment, the substrate is made from paper or paper-based material. In still other embodiments, the substrate is in the shape of a rectangular strip, with the first and second ends being opposed to each other. In a further embodiment, the substrate is a rectangular test strip.

In an embodiment, the "paper" or "paper-based material" is an amalgamation of plant fibers composed of cellulose. In an embodiment, the plant fibers are from wood pulp from pulpwood trees. In an embodiment, the plant fibers are from pulpwood, cotton, hemp, linen and rice, or a mixture thereof. While the fibers used are usually natural in origin, it is an embodiment that a wide variety of synthetic fibers, such as polypropylene and polyethylene, are incorporated into the paper as a way of imparting desirable physical properties. In embodiments, the paper is hydrophilic or hydrophobic, has a surface coating and/or incorporates fillers that provide desirable physical properties prior to coating with the inkjet deposited or spotting of the one or more concatemeric nucleic acid molecules.

In an embodiment, the printing of the reporter layer on the substrate is performed using inkjet printing. In an embodiment, the inkjet printing is thermal ink-jet printing. Any inject printer may be used for printing of the one or more reporter layers on the substrate. In an embodiment, the inject printer in equipped with means to control the location of the inks being printed. In an embodiment the printer is a thermal ink-jet printer. In an embodiment, the printer is an industrial inject printer which deposit more material per pass. Thermal printers can print aqueous inks with properties similar to water. The biosensors of the present application comprise concatemer bioinks with viscosity and surface tension properties similar to aqueous inks (see Table 2). In an embodiment, each different concatemeric solution is printed using a separate printing cartridge.

In an embodiment, the reporter layer is comprised of multiple layers of the concatemeric nucleic acid molecules and one or more molecules for detection on the substrate. In a further embodiment, the reporter layer is comprised of about 1 to about 100 layers, about 5 to about 20 layers, or about 10 to about 15 layers, of the concatemeric nucleic acid molecules and one or more molecules for detection.

In an embodiment, more than one reporter layer is printed on a substrate. In a further embodiment, negative control layers and/or positive control layers are also printed on the same substrate. In a further embodiment, the substrate further comprises markings, printed using regular ink from a separate cartridge, that, for example, label each layer and/or delinate each layer. In a further embodiment, the reporter layers are printed in a specific pattern, for example, in the shape of a plus sign to indicate a positive result. In this example a corresponding negative control is optionally printed in the shape of a minus sign to indicate a negative result.

The versatility offered by combining the control of specific deposition of aptamer bioinks from printing and the direct immobilization of one or more reporter layers on a substrate is applied to multiplexing assays. This allows for simultaneous measurements of one or more analytes in a single run/cycle of the assay. Accordingly it is an embodiment that two or more different reporter layers, each comprising different concatemeric nucleic acids and reporter molecules for different analytes, are printed on the substrate.

The present application also includes assay methods that utilize the biosensor of the present application. In an embodiment, the assay is a method of detecting one or more analytes in a sample, wherein the sample comprises or is suspected of comprising the one or more analytes, the method comprising contacting the sample with the biosensor of the application and monitoring the one or more molecules for detection for a positive or negative result, wherein a positive result indicates the presence of the one or more analytes in the sample. In an embodiment of the application, the one or more molecules for detection comprises a fluorescent molecule and the positive result is a presence of a fluorescent signal on the biosensor.

The sample may be from any source, for example, any biological (for example human or animal medical samples), environmental (for example water or soil) or natural (for example plants) source, or from any manufactured or synthetic source (for example food or drinks). It is most convenient for the sample to be a liquid or dissolved in a suitable solvent to make a solution. For quantitative assays, the amount of sample in the solution should be known. The sample is one that comprises or is suspected of comprising one or more analytes.

In an embodiment, the analyte is selected from metal ions, small molecule drugs, hormonal growth factors, biomolecules, toxins, peptides, proteins, microorganisms, cells and tissues. In another embodiment, the analyte is selected from small molecule drugs, hormonal growth factors, biomolecules, peptides, proteins, bacteria, viruses and cells. In a further embodiment, the analyte is selected from hormonal growth factors and biomolecules. In a further embodiment, the analyte is a biomolecule. In a further embodiment, the analyte is a hormonal growth factor. In yet a further embodiment, the analyte is adenosine triphosphate. In yet a further embodiment, the analyte is platelet-derived growth factor.

EXAMPLES

The following non-limiting examples are illustrative of the present application:

Example 1: Development of Bioactive Paper Sensors of Concatemeric Nucleic Acid Molecules Using Thermal Inkjet-Printing Materials:

Standard and functionalized DNA oligonucleotides were synthesized and purified by HPLC by Integrated DNA Technologies (Coralville, Iowa). Adenosine 5'-triphosphate (ATP), cytidine 5'-triphosphate (CTP), guanosine 5'-triphosphate (GTP), uridine 5'-triphosphate (UTP), T4 polynucleotide kinase (PNK; with 10× reaction buffer A: 500 mM Tris.HCl, 100 mM $MgCl_2$, 50 mM dithiothreitol (DTT), 1 mM spermidine at pH 7.6), T4 DNA ligase (with 10×T4 DNA ligase buffer: 400 mM Tris.HCl, 100 mM $MgCl_2$, 100 mM DTT, 5 mM ATP at pH 7.8), 10 mM dNTPs, φ29 DNA polymerase (with 10×φ29 DNA polymerase buffer: 330 mM Tris.acetate, 100 mM Mg.acetate, 660 mM K.acetate, 1% (v/v) Tween 20, 10 mM DTT at pH 7.9), GeneRuler™ 1 kb Plus DNA ladder and 10,000×SYBR Safe DNA gel stain were purchased from Fermentas Life Sciences (Burlington, ON). Recombinant human platelet derived growth factor-BB (PDGF), epidermal growth factor (EGF) and insulin-like growth factor I (IGF-I) were purchased from R&D Systems (Minneapolis, Minn.). All other analytical grade chemicals and solvents were purchased from Sigma-Aldrich (Oakville, ON). Water was purified prior to use with a Millipore Milli-Q Synthesis A10 water purification system.

Preparation of Concatemeric Aptamers:

Concatemers of each structure-switching aptamer were prepared using the following templates: the linear precursors of the circular templates were first ligated using the appropriate ligation template to generate the circular template, which hybridizes with the primer sequences to initiate the RCA process.

```
Linear ATP Aptamer Circular Template:
                                       [SEQ ID NO: 1]
5'-TGTCT TCGCC TATAG TGAAC CTTCC TCCGC AATAC
TCCCC CAGGT ATCTT TCGAC TAAGC ACC-3'

ATP Aptamer Ligation Template:
                                       [SEQ ID NO: 2]
5'-GGCGA AGACA GGTGC TTAGT C-3'

ATP Aptamer Primer:
                                       [SEQ ID NO: 3]
5'-GGGGG AGTAT TGCGG AGGAA-3'

Linear PDGF Aptamer Circular Template:
                                       [SEQ ID NO: 4]
5'-TGCAG CGACT CACAG GATCA TGGTG ATGCT CTACG
TGCCG TAGCC TGCCC TTTCG ACTAC C-3'

PDGF Aptamer Ligation Template:
                                       [SEQ ID NO: 5]
5'-GAGTC GCTGC AGGTA GTCGA A-3'

PDGF Aptamer Primer
                                       [SEQ ID NO: 6]
5'-CGTAG AGCAT CACCA TGATC-3'
```

Circularization of the linear templates to form circular templates for RCA began with phosphorylating 800 pmol of the linear templates in 1× reaction buffer A using 10 U of T4 PNK with 100 nmol of ATP and incubating at 37° C. for 30 min followed by heating at 90° C. for 5 min to inactivate the enzyme and cooling to room temperature. In order to ligate the circle together, 1 nmol of the ligation template was added and then heated at 90° C. for 1 min. Once cooled to room temperature, 15 U of T4 DNA ligase was added to the mixture and incubated at room temperature for 12 h in 1× ligase buffer.

The circularized templates were precipitated with ethanol before purifying by 10% polyacrylamide denaturing (8M urea) gel electrophoresis (dPAGE), from which only the circular sequences were isolated and eluted from the gel, precipitated with ethanol and resuspended in water for quantification using a NanoVue spectrophotometer (absorbance at 260 nm).

The RCA reaction of each of the aptamer sequences was carried out using 10 pmol of circular template with 10 pmol of primer in water (36.5 μL total volume) and heating this mixture at 90° C. for 1 min. Following cooling, 5 μL of 10×ϕ29 polymerase buffer, 2.5 μL of 10 mM (each) dNTPs and 10 U of ϕ29 polymerase were added to the reaction mixture and allowed to incubate at 30° C. for 1 h. The reaction was followed by a 5-fold dilution with water before heating at 90° C. for 5 min to deactivate the enzyme. Control experiments were also performed without circular template. Concatemeric aptamers from the reaction mixture were purified by centrifugation using a 100 kDa Nanosep® spin column and quantified using a NanoVue spectrophotomer (absorbance at 260 nm). Visualization of the concatemeric aptamers was performed using a 0.6% agarose gel (w/v) with a SYBR safe DNA stain. The gel was imaged using a Typhoon Trio+ Variable Mode Imager (488 nm excitation, 526 nm emission, 600 PMT, 3 mm focal plane, medium sensitivity and 200 micron resolution). As the exact size of the concatemeric aptamer is unknown, an approximate molar concentration using the absorbance at 260 nm of the concatemeric aptamer was calculated based on one repeat of the aptamer sequence. Therefore, the concentration of the aptamer sequence units in the concatemer is equivalent to that of the monomeric construct in all subsequent studies.

Preparation of DNA Aptamer Reporter Complexes:

The structure-switching, fluorescence-signaling aptamer reporter complexes for ATP- and PDGF-binding were prepared as described below. Fluorophore-labeled oligonucleotides (FDNA) hybridize to the italicized nucleotides for both the monomeric and concatemeric aptamers, while quencher-labeled oligonucleotides (QDNA) hybridize to the nucleotides in bold for both the monomeric and concatemeric aptamers. The 'no hybridization' QDNA (NH-QDNA) lacks complementarity and should not hybridize to any of the aptamer constructs.

```
FDNA for ATP aptamer (ATP-FDNA):
                                       [SEQ ID NO: 7]
5'-(fluorescein)CGACT AAGCA CCTGT C-3'

QDNA for ATP aptamer (ATP-QDNA):
                                       [SEQ ID NO: 8]
5'-CCCAG GTATC TT(dabcyl)-3'

Monomeric ATP aptamer construct, tripartite
version (ATP-Apt-Tri):
                                       [SEQ ID NO: 9]
5'-TCACT ATAGG CGAAG ACAGG TGCTT AGTCG AAAGA
TACCT GGGGG AGTAT TGCGG AGGAA GGT-3'

Monomeric ATP aptamer construct, bipartite
version (ATP-Apt-Bi):
                                       [SEQ ID NO: 10]
5'-TTTTT TTTTT(fluorescein) TCACT GACCT GGGGG
AGTAT TGCGG AGGAA GGT-3'

FDNA for PDGF aptamer (PDGF-FDNA):
                                       [SEQ ID NO: 11]
5'-(fluorescein)GACTA CCTGC AGCGA-3'

QDNA for PDGF aptamer (PDGF-QDNA):
                                       [SEQ ID NO: 12]
5'-AGCCT GCCCT TT(dabcyl)-3'

Monomeric PDGF aptamer construct (PDGF-Apt):
                                       [SEQ ID NO: 13]
5'-TGAGT CGCTG CAGGT AGTCG AAAGG GCAGG CTACG
GCACG TAGAG CATCA CCATG ATCCT G-3'

No hybridization QDNA (NH-QDNA):
                                       [SEQ ID NO: 14]
5'-GGGTC CGTAG GA(dabcyl)-3'
```

Optimization of Concatemer Fluorescence Signaling in Solution:

To determine the optimal ratios of aptamer/FDNA/QDNA required for maximal signal generation, experiments with increasing molar equivalents of FDNA and QDNA to aptamer were performed. Prior to QDNA addition, each concatemeric aptamer and its cognate FDNA were combined in either a 1:1, 2:1 or 3:1 (aptamer:FDNA) molar ratio in the appropriate assay buffer and heated at 90° C. for 5 min, cooled to room temperature and then incubated for 1 h at 25° C. After the 1 h incubation period, baseline fluorescence was measured for 10 min prior to the addition of the proper QDNA to achieve a final concentration of 1, 3, 6, or 9× the number of molar equivalents of FDNA (100 nM final concentration of FDNA). Identical experiments were also carried out in the varying ratios with non-hybridizing (NH)-QDNA or without aptamer addition as controls. These studies were performed in ATP assay buffer (20 mM Tris-HCl, 100 mM NaCl, 5 mM MgCl$_2$ at pH 7.8) for the ATP aptamer or PDGF assay buffer (20 mM Tris-HCl, 140 mM NaCl, 5 mM KCl, 1 mM CaCl$_2$, 1 mM MgCl$_2$ at pH 7.8) for the PDGF aptamer.

Sensitivity and Selectivity of Concatemeric Aptamers:

To test the sensitivity of the concatemeric aptamers, each concatemer complex was combined in the 1:1:6 molar ratio (aptamer, FDNA and QDNA) in the appropriate buffer, heated at 90° C. for 5 min and cooled. Samples were incubated for 1 h at 25° C. Following baseline fluorescence measurements, ATP was then added to the ATP-binding concatemer at final concentrations of 0-3 mM, while PDGF-BB was added to the PDGF-binding concatemer at a final concentrations of 0-300 nM (2 μL at the appropriate concentration). This experiment was also repeated with the monomeric versions of each aptamer, complexed in the same 1:1:6 ratio. To test the ability of the concatemer reporters to bind their specific target over structurally-related molecules, ATP-binding concatemeric aptamers were incubated with ATP, CTP, GTP or UTP at a final concentration of 1 mM following baseline fluorescence measurements, while the concatemeric PDGF aptamer was incubated with PDGF-BB, IGF-1, EGF or BSA at a final concentration of 100 nM.

Paper-Based Assay Fabrication:

In the preliminary paper-based tests using manual deposition of aptamers on paper by pipette, three layers of 0.1 μL were pipetted onto small pieces of Whatman® Grade 1 chromatography paper (7×10 cm) using the ATP-binding concatemeric aptamer reporter (aptamer/FDNA with or without QDNA) in a "cross" pattern consisting of 5 spots. The solutions were then dried on the paper for 30 min, followed by lateral flow of 1 mL of ATP assay buffer up to half the vertical length of paper. These pieces of paper were then allowed to dry flat for 2 h on a non-absorbent plastic surface prior to imaging. Increasing concentrations of ATP were then spotted on each "cross" region (5 μL; 0-3 mM) and imaged after 5 min of drying.

For the inkjet-printed assays, large sheets of Whatman® Grade 1 chromatography paper were cut to standard letter sheet size (8.5×11 inches) in order to be fed into a Canon Pixma MP280 inkjet printer, washed with buffer using vertical flow to decrease background fluorescence and allowed to dry. The black ink cartridge specific for the Canon printer (#210) was opened in order to remove the foam pad with liquid ink, and then the empty reservoir was extensively rinsed with water and dried. The color cartridge (#211) was used as received to print cut lines and labels (cyan) or sensor area outlines (yellow). Patterned templates for printing of both colors and bioinks (using black) were made with Microsoft PowerPoint and were printed using "high" quality with the "color only" or "black only" ink cartridge setting when using these inks, respectively. A bioink consisted of either the ATP- or PDGF-binding concatemeric reporter complex (aptamer/FDNA with or without QDNA) or the ATP-binding monomeric aptamers (tripartite construct with FDNA and bipartite construct)—up to 600 μL can be added to the cartridge. Following the printing of each different bioink, the black cartridge was extensively rinsed with water and dried (alternatively, different cartridges can be used for the various bioinks). Completed assay pages made by feeding the paper through the printer multiple times (to create 3-15 layers) were allowed to dry for 5 min and cut following the printed color lines. In the multiplexing assay, increasing layers of the ATP-binding concatemeric aptamer/FDNA (no QDNA) were printed as reference guides to depict the signal intensities expected for each test reporter upon target addition. Since the PDGF-binding aptamer produces a lower signal enhancement than that of the ATP-binding aptamer (see below), fewer layers were used to produce lower intensity references. The number of print layers used for the signal reference guides are as follows: 3 layers in "0", 6 or 4 layers in "Lo", 10 or 6 layers in "Med" and 12 or 8 layers in "Hi" for indicating the ATP- or PDGF-binding aptamers, respectively.

For the ATP aptamer adsorption comparison test, printed and cut paper pieces were placed in a trough containing 1 mL of assay buffer (alone, with 0.1% (w/v) Triton-X 100, or 1% (w/v) BSA) and the solution was allowed to flow to up to half the vertical length of paper. These pieces of paper were then allowed to dry flat for 2 h on a non-absorbent plastic surface prior to imaging. For signal response assays, the appropriate target or buffer only was added using 5 μL of solution deposited directly on the paper surface where the bioinks were printed and imaged after 5 min of drying. All tests were performed at room temperature (~22° C.).

Surface Tension and Viscosity Measurements:

Viscosity was measured for 10 mL samples of each bioink and assay buffer using a Sine-Wave Vibro Viscometer (SV-10) at ~20° C. following calibration with Milli-Q water (viscosity≈1 cP). Dynamic surface tension from drop shape and contour analysis was performed using the Pendant Drop Method using an optical contact angle (OCA) 35 instrument with SCA22 software. Pendant drops were formed by a dosing needle with an outer diameter of 2.41 mm, which was connected to a 1-mL glass syringe, and measured at 22° C. Milli-Q water with a surface tension of 72.8-72.0 mN/m at 20-25° C.[2] was used for calibration.

Fluorescent Intensity Measurements:

All solution-based fluorescence intensity measurements were performed using a Tecan Infinite® M1000 plate reader in fluorescence mode. Samples were excited at 490 nm (5-nm bandpass) and emission measured at 520 nm (5-nm bandpass) with a 20 μs integration time using the bottom-read setting. All measurements were acquired at 25° C. Kinetic measurements were performed to assess FNA response to addition of a given species (i.e. QDNA, targets, etc.) using fluorescence intensity reads every minute for both baseline measurements (no QDNA/target; 10 min) and after addition of QDNA for a total of 1 h or target for 30 min, with orbital shaking of 2.5 mm amplitude for 5 s between each measurement to ensure proper mixing. All assays were carried out in triplicate with background fluorescence subtraction. Raw fluorescence measurements were normalized to fluorescence enhancement or F/F$_o$ where F is the endpoint fluorescence intensity and F$_o$ is the initial fluorescence intensity prior to QDNA/target addition.

Fluorescent Lifetime Measurements:

All fluorescence lifetime measurements were obtained using a Tecan Ultra Evolution plate reader with an FLT attachment. Samples were excited at 440 nm with a pulsed diode laser operating at 40 MHz and emission was measured at 544 nm (25-nm bandwidth) for a 1000 ms acquisition time. Five different types of sample were prepared in triplicate for each aptamer: one sample containing FDNA only, samples with either the concatemeric or monomeric aptamer with only FDNA and those prepared with either concatemeric aptamer or monomeric aptamer combined with both FDNA and QDNA. All samples were prepared in their respective assay buffer, heated at 90° C. for 5 min, cooled to room temperature and then incubated at the appropriate assay temperature for 1 h. Fluorescence lifetime measurements were then obtained at 25° C. (no target). Target analyte for each aptamer was then added (1 mM ATP or 100 nM PDGF-BB final concentration) and the fluorescence lifetimes were measured again after 30 min. These fluorescence intensity decays were analyzed using Magellan software with fitting to a multi-exponential model:[3]

$$I(t) = \Sigma_i \alpha_i \exp(-t/\tau_i) \tag{1}$$

where $\tau_i$ are the decay times and $a_i$ are the pre-exponential factors (amplitudes) of the individual components ($\Sigma \alpha_i = 1$). The fractional contribution of each component to the steady state intensity is given by:

$$f_i = \frac{\alpha_i \tau_i}{\Sigma_j \alpha_j \tau_j} \tag{2}$$

The amplitude-weighted lifetime is given by:

$$\langle \tau \rangle = \Sigma_i \alpha_i \tau_i \tag{3}$$

and the intensity-weighted average lifetime is given by:

$$\bar{\tau} = \Sigma_i f_i \tau_i \tag{4}.$$

Fluorescence Imaging:

All fluorescence images (for paper-based assays) were acquired using a ChemiDoc MP Imaging System with UV trans illumination, a standard filter (filter 1) and 0.1 s exposure time. Image color has been artificially set to SYBR Green. Pixel intensity analysis was performed using the volume tools of the ImageLab software to create rectangles around the printed boxed shapes. The relative pixel intensity was calculated using the average pixel intensity obtained from rectangles around the boxed "x" positive controls as the 100% value and the average pixel intensity obtained from rectangles around the boxed "✓" without target added (negative control) as 0%. It should be noted, however, that the pixel analysis provides a slight undervaluation of the "✓" intensity as it occupies ~80% of the volume of the "x".

Results & Discussion

Figure 1:
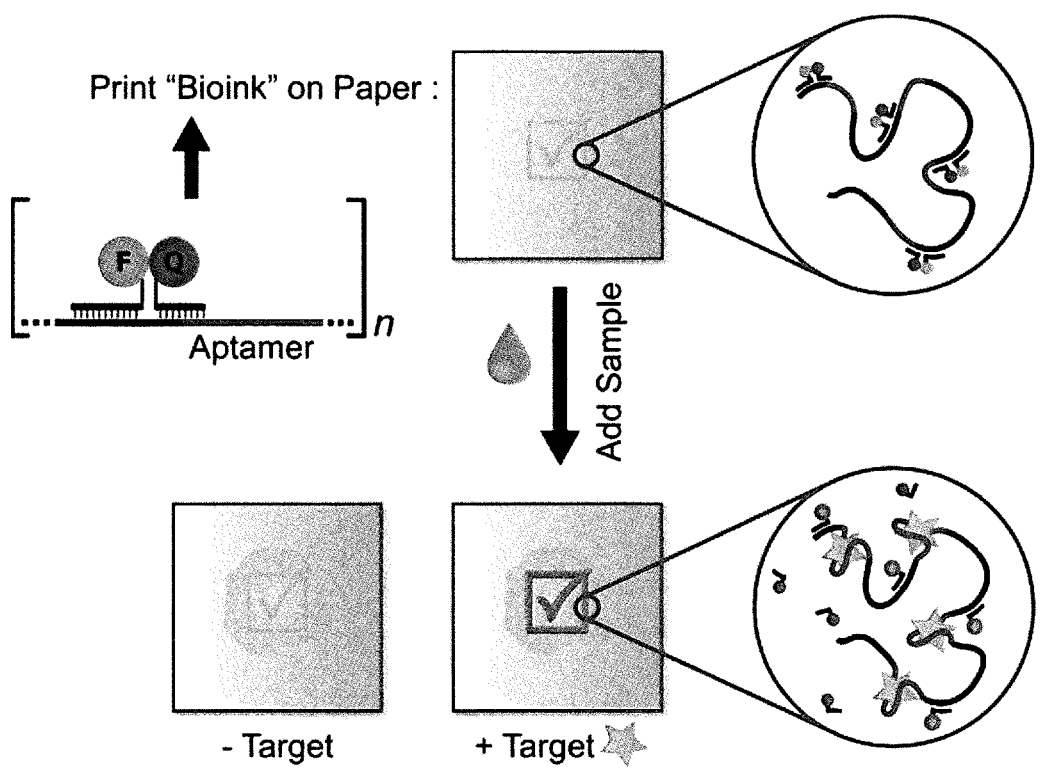
FIG. 1 is a schematic representation of one embodiment of a paper sensor of the application inkjet-printed with concatemeric fluorescence-signaling aptamers.

FIG. 1 schematically illustrates one embodiment of an approach wherein concatemeric DNA aptamers are allowed to hybridize with two short DNA strands—FDNA and QDNA—labeled respectively with a fluorophore and matching quencher in order to function as optical structure-switching reporters[11] on a paper substrate.

Preparation of Concatemeric Aptamers:

Two different concatemeric structure-switching aptamer reporters were produced, using model aptamers for adenosine triphosphate (ATP) and platelet-derived growth factor (PDGF), respectively.[12] These aptamers were not only chosen for the ability to bind their cognate targets at biologically relevant levels[13] but also as well-characterized representative aptamers for small molecule and protein detection. The complementary sequence for each aptamer is encoded into a circular template designed to generate two different sequence elements: the DNA aptamer that partially binds the QDNA, and a spacer that binds FDNA. Successful preparation of both concatemers was confirmed by agarose gel electrophoresis, with a band for each sequence above the 20,000 base-pair marker, corresponding to several megadaltons in size or hundreds to thousands of aptamer repeats in tandem.

Preparation of DNA Aptamer Reporter Complexes and Optimization of Concatemer Fluorescence Signaling in Solution:

The molar ratios of FDNA and QDNA to bind to the concatemers were optimized in order to construct the pre-quenched duplex. In the original tripartite monomeric reporter, a 2:1:3 ratio of aptamer/FDNA/QDNA was used to ensure that the majority of FDNA would anneal to the aptamer and also engage QDNA for proper quenching and low background signal levels prior to target binding.[11a] However, it was found that using a 1:1 aptamer/FDNA ratio with excess QDNA (6×FDNA concentration) provided the greatest amount of quenching (FIG. 7). Constructs using QDNA and FDNA alone in solution (without the aptamer unit) or a scrambled QDNA with no complementarity to either aptamer were unable to generate any signal reduction, indicating that quenching was the result of proper hybridization to the concatemeric aptamers.

Figure 2:
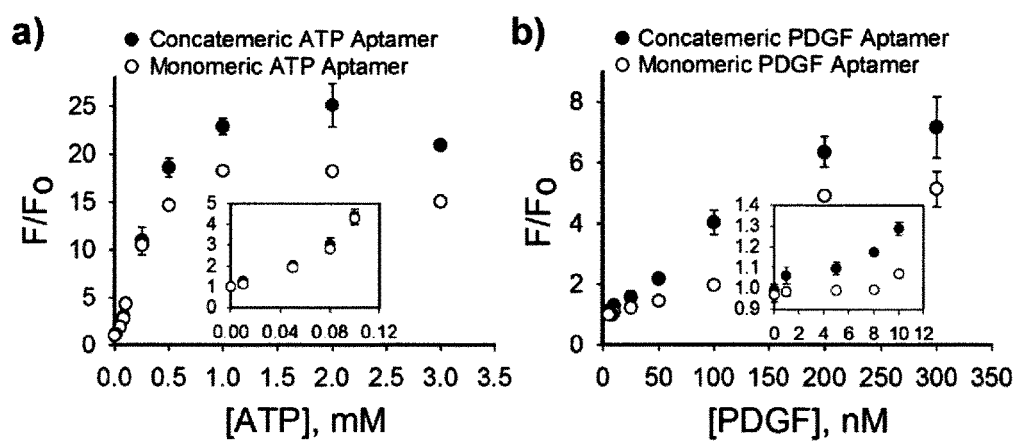
FIG. 2 shows the fluorescence response of (A) ATP aptamers, and (B) PDGF aptamers with cognate target added in solution in an exemplary embodiment of the application.

Sensitivity and Selectivity of Concatemeric Aptamers:

We then evaluated whether the concatemeric aptamer constructs could undergo structure switching while maintaining the sensitivity and selectivity of the original monomers. The results revealed that each concatemeric reporter provided a target concentration-dependent response similar to that of the monomeric reporter, but with a greater relative signal enhancement, particularly at higher target concentrations (FIG. 2). Fluorescence lifetime measurements (Table 1) showed that the enhanced signal generation arose from dynamic quenching of FDNA in the concatemer, which would be expected from bringing quenchers non-adjacent to a given fluorophore closer in space if the concatemer folds upon itself, adding to the static quenching obtained in both the monomeric and concatemeric constructs. Importantly, the concatemeric aptamers also retained their expected selectivity and did not produce any measurable change in signal with similar but non-intended targets (FIG. 8).

Paper-Based Assay Fabrication:

Preliminary studies involved pipetting the concatemeric aptamers on paper by hand (FIG. 9), but this proved to be too slow and irreproducible. To address these issues, the aptamer reporters were printed on paper using a Canon office inkjet printer (thermal printhead) by replacing the content of the black ink cartridge with the aptamer bioink. Although the printed bioinks are invisible, the color cartridge is available to print cut lines and labels for precise fabrication—examples are shown in FIG. 10. A consumer thermal inkjet printer was chosen for this study since it is generally cheaper and more accessible than piezoelectric inkjet printers. Furthermore, piezoelectric printers require a narrow window of viscosity and surface tension (ex. 3-10 cP and 20-40 mN/m), making it necessary to optimize additives to control these factors, while thermal printers can print aqueous inks with properties similar to water;[14] Table 2 provides the viscosity and surface tension of the aptamer bioinks.

For the paper adsorption assays, the movement of "+" shapes printed using the concatemeric ATP aptamer/FDNA reporter (denoted "RCA" in FIG. 3) was compared to that of the monomeric aptamer/FDNA ("Tri" in FIG. 3) following lateral flow using three assay solutions: buffer alone ("Buffer"), buffer with 0.1% Triton-X 100 ("0.1Trix") and buffer with 1% BSA ("1BSA"). As seen in FIG. 3, increasing the number of passes through the printer to make multiple layers of each bioink resulted in better signal intensity. After washing by wicking different buffer solutions, the monomeric construct was either highly smeared or completely delocalized from its initial position, whereas the concatemers remained in place.

Buffer solutions containing either Triton-X 100 or BSA were chosen to demonstrate the strength of adsorption despite the use of standard washing or blocking agents. FIG. 11 also shows that the effects of lateral flow on a bipartite version of the monomeric construct, in which the fluorophore is covalently bound (to avoid dehybridization and elution of FDNA alone), are similar to the tripartite version of the monomeric aptamer, indicating the delocalization of the entire aptamer unit on paper.

To confirm the fluorescence response of printed concatemers on paper and aid in sensor design, the full reporter system (aptamer/FDNA/QDNA) for ATP detection was printed using a boxed "✓", while the construct with the aptamer/FDNA only, acting as the positive control, was printed with a boxed "x". 15 layers of aptamer bioinks were printed and provided the highest fluorescence signal in the lateral flow tests, 15-layer printing was used for all subsequent assays allowing us to produce 160 sensors per hour per printer (32 sensors per page). Industrial inkjet printers can deposit far more material per pass, which may allow single pass printing once the method is scaled up. It can be observed in FIG. 4 that the concatemeric aptamer reporter appears less diffuse after printing and drying when compared to the monomeric version. After spotting either the assay buffer alone or that containing 2 mM ATP onto the printed areas, signal enhancement of the full complex was only observed in the concatemeric aptamer checkmark, whereas the monomeric aptamer checkmark became delocalized. While the signal response assay also functioned in a lateral flow format (data not shown), it was found that the method of spotting sample on the paper decreased both the assay time (flow and drying) and the sample volume required, and was thus adopted in subsequent assay designs.

Continuing with the boxed "x" and "✓" format, the response upon adding a concentration gradient of ATP to the printed concatemer reporter was assessed. FIG. 5 demonstrates the relative emission intensity after spotting target with increasing concentrations from left to right. Visualization of the fluorescence output demonstrated increasing fluorescence intensity of the checkmarks with increasing ATP concentrations, while quantitative pixel intensity analysis revealed a detection limit and dynamic range consistent with that observed in solution. We conducted the same experiment with the PDGF aptamer reporters printed on paper, and as shown in FIG. 12, the concatemeric PDGF reporter system behaved very similarly to the ATP reporter. These results indicate that our approach is generally applicable to both small molecule and protein-binding DNA aptamers.

The versatility offered by combining the control of specific deposition from inkjet printing and the direct immobilization of our concatemeric bioinks on paper was also tested by creating a multiplexing assay with internal references for quantification. Since the patterning of letters allows for the simplest signal readout with results presented as text,[15] multiplexing was achieved by printing the letters "A" and "P" to differentially denote the ATP reporter and PDGF reporter, respectively. Reference guides, which consisted of increasing numbers of layers of the ATP concatemer/FDNA only, depicting signal intensities expected for different levels of each target, were printed bordering the letters using "0", "Lo", 'Med" and "Hi". After spotting either 2 mM ATP or 200 nM PDGF to the printed area, only the appropriate letter displays a signal enhancement similar to the adjacent reference guide, while no signaling occurs with buffer alone (FIG. 6).

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Intensity-weighted fluorescence lifetimes (ns) of concatemeric and monomeric aptamers in solution.

| | ATP Aptamer | | PDGF Aptamer | |
|---|---|---|---|---|
| Sample | −Target | +Target | −Target | +Target |
| FDNA only | 4.04 ± 0.04 | 4.01 ± 0.04 | 3.78 ± 0.05 | 3.79 ± 0.05 |
| Monomeric aptamer + FDNA | 4.21 ± 0.07 | 4.19 ± 0.08 | 3.86 ± 0.05 | 4.07 ± 0.08 |
| Monomeric aptamer + FDNA + QDNA | 3.9 ± 0.1 | 3.97 ± 0.03 | 3.6 ± 0.3 | 3.8 ± 0.1 |
| Concatemeric aptamer + FDNA | 4.27 ± 0.06 | 4.16 ± 0.04 | 3.73 ± 0.03 | 3.77 ± 0.05 |
| Concatemeric aptamer + FDNA + QDNA | 3.1 ± 0.6 | 3.9 ± 0.2 | 2.9 ± 0.1 | 3.6 ± 0.1 |

TABLE 2

Viscosities and surface tensions of concatemeric and monomeric aptamers in solution.

| | Viscosity (cP) | Surface Tension (mN/m) |
|---|---|---|
| ATP Aptamer Buffer | 1.07 ± 0.01 | 70.1 ± 0.8 |
| Monomeric ATP Aptamer Solution | 1.07 ± 0.01 | 70.4 ± 0.6 |
| Concatemeric ATP Aptamer Solution | 1.06 ± 0.01 | 70.6 ± 0.4 |
| PDGF Aptamer Buffer | 1.04 ± 0.01 | 70.2 ± 0.7 |
| Monomeric PDGF Aptamer Solution | 1.05 | 69.9 ± 0.8 |
| Concatemeric ATP Aptamer Solution | 1.04 ± 0.01 | 70.5 ± 0.6 |
| Water[a] | 1.00 | 72.8 |

[a]International Association for the Properties of Steam (IAPS) values for viscosity and surface tension of water at 20° C.

REFERENCES 1. a) Martinez, A. W., Phillips, S. T., Butte, M. J., Whitesides, G. M. *Angew. Chem. Int. Ed.* 2007, 46, 1318-1320; b) Pelton, R. *Trends Anal. Chem.* 2009, 28, 925-942; c) Martinez, A. W., Phillips, S. T., Whitesides, G. M., Carrilho, E. *Anal. Chem.* 2010, 82, 3-10; d) Liana, D. D., Raguse, B., Gooding, J. J., Chow, E. *Sensors.* 2012, 12, 11505-11526; e) Yetisen, A. K., Akram, M. S., Lowe, C. R. *Lab Chip.* 2013, 13, 2210-2251.

2. a) Stollner, D., Scheller, F. W., Warsinke, A. *Anal. Biochem.* 2002, 304, 157-165; b) Su, S., Nutiu, R., Filipe, C. D., Li, Y., Pelton, R. *Langmuir* 2007, 23, 1300-1302; c) Araujo, A. C., Song, Y., Lundeberg, J., Stahl, P. L., Brumer, H., 3rd *Anal. Chem.* 2012, 84, 3311-3317; d) Filpponen, I., Kontturi, E., Nummelin, S., Rosilo, H., Kolehmainen, E., Ikkala, O., Laine, J. *Biomacromolecules* 2012, 13, 736-742; e) Yu, A., Shang, J., Cheng, F., Paik, B. A., Kaplan, J. M., Andrade, R. B., Ratner, D. M. *Langmuir* 2012, 28, 11265-11273; f) Noor, M. O., Shahmuradyan, A., Krull, U. J. *Anal. Chem.* 2013, 85, 1860-1867.
3. a) Hossain, S. M. Z., Luckham, R. E., Smith, A. M., Lebert, J. M., Davies, L. M., Pelton, R. H., Filipe, C. D. M., Brennan, J. D. *Anal. Chem.* 2009, 81, 5474-5483; b) Hossain, S. M. Z., Brennan, J. D. *Anal. Chem.* 2011, 83, 8772-8778; c) Hossain, S. M. Z., Ozimok, C., Sicard, C., Aguirre, S., Ali, M. M., Li, Y., Brennan, J. *Anal. Bioanal. Chem.* 2012, 403, 1567-1576; d) Wang, J., Bowie, D., Zhang, X., Filipe, C., Pelton, R., Brennan, J. D. *Chem. Mater.* 2014, 26, 1941-1947.
4. a) Martinez, A. W., Phillips, S. T., Whitesides, G. M. *Proc. Natl. Acad. Sci. U.S.A.* 2008, 105, 19606-19611; b) Klasner, S. A., Price, A. K., Hoeman, K. W., Wilson, R. S., Bell, K. J., Culbertson, C. T. *Anal. Bioanal. Chem.* 2010, 397, 1821-1829; c) Abe, K., Suzuki, K., Citterio, D. *Anal. Chem.* 2008, 80, 6928-6934; d) Li, X., Tian, J., Garnier, G., Shen, W. *Colloids Surf., B* 2010, 76, 564-570; e) Li, X., Tian, J., Nguyen, T., Shen, W. *Anal. Chem.* 2008, 80, 9131-9134; (f) Olkkonen, J., Lehtinen, K., Erho, T. *Anal. Chem.* 2010, 82, 10246-10250; (g) Maattanen, A., Fors, D., Wang, S., Valtakari, D., Ihalainen, P., Peltonen, J. *Sens. Actuators, B* 2011, 160, 1404-1412. f) Dungchai, W., Chailapakul, O., Henry, C. S. *Analyst* 2011, 136, 77-82.
5. a) Ellington, A. D., Szostak, J. W. *Nature* 1990, 346, 818-822; b) Tuerk, C., Gold, L. *Science* 1990, 249, 505-510; c) Navani, N. K., Li, Y. F. *Curr. Opin. Chem. Biol.* 2006, 10, 272-281; d) Shangguan, D., Li, Y., Tang, Z., Cao, Z. C., Chen, H. W., Mallikaratchy, P., Sefah, K., Yang, C. J., Tan, W. *Proc. Natl. Acad. Sci. U.S.A.* 2006, 103, 11838-11843; e) Liu, J., Cao, Z., Lu, Y. *Chem. Rev.* 2009, 109, 1948-1998.
6. a) Breaker, R. R. *Curr. Opin. Chem. Biol.* 1997, 1, 26-31; b) Wilson, D. S., Szostak, J. W. *Annu. Rev. Biochem.* 1999, 68, 611-647; c) Famulok, M., Mayer, G., Blind, M. *Acc. Chem. Res.* 2000, 33, 591-599; d) Famulok, M., Hartig, J. S., Mayer, G. *Chem. Rev.* 2007, 107, 3715-3743; e) Song, S. P., Wang, L. H., Li, J., Zhao, J. L., Fan, C. H. *Trends Anal. Chem.* 2008, 27, 108-117; f) Sefah, K., Phillips, J. A., Xiong, X., Meng, L., Van Simaeys, D., Chen, H., Martin, J., Tan, W. *Analyst* 2009, 134, 1765-1775.
7. a) Su, S., Ali, M. M., Filipe, C. D., Li, Y., Pelton, R. *Biomacromolecules* 2008, 9, 935-941; b) Liu, H., Xiang, Y., Lu, Y., Crooks, R. M. *Angew. Chem. Int. Ed.* 2012, 51, 6925-6928; c) Ge, L., Wang, P., Ge, S., Li, N., Yu, J., Yan, M., Huang, J. *Anal. Chem.* 2013, 85, 3961-3970; d) Yan, J., Yan, M., Ge, L., Yu, J., Ge, S., Huang, J. *Chem. Commun.* 2013, 49, 1383-1385; (e) Evans, E., Gabriel, E. F., Benavidez, T. E., Tomazelli Coltro, W. K., Garcia, C. D. *Analyst* 2014, 139, 5560-5567.
8. a) Fire, A., Xu, S. Q. *Proc. Natl. Acad. Sci. U.S.A.* 1995, 92, 4641-4645; b) Liu, D. Y., Daubendiek, S. L., Ziliman, M. A., Ryan, K., Kool, E. T. *J. Am. Chem. Soc.* 1996, 118, 1587-1594; c) Ali, M. M., Li, F., Zhang, Z., Zhang, K., Kang, D. K., Ankrum, J. A., Le, X. C., Zhao, W. *Chem. Soc. Rev.* 2014, 43, 3324-3341.
9. a) Lizardi, P. M., Huang, X. H., Zhu, Z. R., Bray-Ward, P., Thomas, D. C., Ward, D. C. *Nat. Genet.* 1998, 19, 225-232; b) Di Giusto, D. A., Wlassoff, W. A., Gooding, J. J., Messerle, B. A., King, G. C. *Nucleic Acids Res.* 2005, 33; c) Cho, E. J., Yang, L. T., Levy, M., Ellington, A. D. *J. Am. Chem. Soc.* 2005, 127, 2022-2023; d) Tian, Y., He, Y., Mao, C. D. *ChemBioChem* 2006, 7, 1862-1864; e) Cheglakov, Z., Weizmann, Y., Basnar, B., Willner, I. *Org. Biomol. Chem.* 2007, 5, 223-225; f) Yang, L. T., Fung, C. W., Cho, E. J., Ellington, A. D. *Anal. Chem.* 2007, 79, 3320-3329; g) Ali, M. M., Li, Y. *Angew. Chem. Int. Ed.* 2009, 48, 3512-3515; h) Zhao, W., Cui, C. H., Bose, S., Guo, D., Shen, C., Wong, W. P., Halvorsen, K., Farokhzad, O. C., Teo, G. S., Phillips, J. A., Dorfman, D. M., Karnik, R., Karp, J. M. *Proc. Natl. Acad. Sci. U.S.A.* 2012, 109, 19626-19631.
10. a) Zhao, W., Gao, Y., Kandadai, S. A., Brook, M. A., Li, Y. *Angew. Chem. Int. Ed.* 2006, 45, 2409-2413; b) Zhao, W., Gao, Y., Brook, M. A., Li, Y. *Chem. Commun.* 2006, 3582-3584; c) Cheglakov, Z., Weizmann, Y., Braunschweig, A. B., Wilner, O. I., Willner, I. *Angew. Chem. Int. Ed.* 2008, 47, 126-130; d) Zhang, Z., Eckert, M. A., Ali, M. M., Liu, L., Kang, D. K., Chang, E., Pone, E. J., Sender, L. S., Fruman, D. A., Zhao, W. *ChemBioChem* 2014, 15, 1268-1273.
11. a) Nutiu, R., Li, Y. *J. Am. Chem. Soc.* 2003, 125, 4771-4778; b) Nutiu, R., Li, Y. *Chem. Eur. J.* 2004, 10, 1868-1876; c) Nutiu, R., Li, Y. *Methods* 2005, 37, 16-25.
12. a) Huizenga, D. E., Szostak, J. W. *Biochemistry* 1995, 34, 656-665; b) Green, L. S., Jellinek, D., Jenison, R., Ostman, A., Heldin, C. H., Janjic, N. *Biochemistry* 1996, 35, 14413-14424.
13. a) Beis, I., Newsholme, E. A. *Biochem. J.* 1975, 152, 23-32; (b) Huang, J. S., Huang, S. S., Deuel, T. F. *J. Cell. Biol.* 1983, 97, 383-388.
14. a) Calvert, P. *Chem. Mater.* 2001, 13, 3299-3305; (b) de Gans, B. J., Duineveld, P. C., Schubert, U.S. *Adv. Mater.* 2004, 16, 203-213; (c) Di Risio, S., Yan, N. *Macromol. Rapid Commun.* 2007, 28, 1934-1940; d) Gonzalez-Macia, L., Morrin, A., Smyth, M. R., Killard, A. J. *Analyst* 2010, 135, 845-867; e) Komuro, N., Takaki, S., Suzuki, K., Citterio, D. *Anal. Bioanal. Chem.* 2013, 405, 5785-5805.
15. Li, M., Tian, J., Al-Tamimi, M., Shen, W. *Angew. Chem. Int. Ed.* 2012, 51, 5497-5501.

The invention claimed is:

1. A biosensor for detecting an analyte comprising:
   a) a paper or paper-based substrate; and
   b) one or more reporter layers absorbed on the paper or paper-based substrate, each of the one or more reporter layers comprising one or more concatemeric nucleic acid molecules comprised of tandem repeating aptamers and one or more reporter nucleic acid molecules for detection of the analyte,
   the one or more concatemeric nucleic acid molecules having a molecular weight that (i) immobilizes the concatemeric nucleic acid molecules to the paper or paper-based substrate and (ii) is from about 1,000,000 to 1,000,000,000 Da,
   wherein the one or more reporter layers are absorbed on the paper or paper-based substrate by non-chemical means selected from printing and spotting.

2. The biosensor of claim 1, wherein the nucleic acid aptamers comprise a first nucleic acid sequence that is complimentary to a first reporter nucleic acid molecule and a second nucleic acid sequence that is complimentary to a second reporter nucleic acid molecule, wherein the first reporter nucleic acid molecule comprises a fluorescent molecule and the second reporter nucleic acid molecule comprises a corresponding quencher molecule for the fluorescent molecule and the first nucleic acid sequence and the second nucleic acid sequence are located on the nucleic acid aptamer at positions wherein the fluorescence of the fluorescent molecule is quenched by the quenching molecule in the absence of analyte.

3. The biosensor of claim 2, wherein in the presence of analyte, the quenching molecule is displaced resulting in fluorescence.

4. The biosensor of claim 1 comprising:
   a) the paper or paper-based substrate having a first end and second end;
   b) one or more reporter layers absorbed on the substrate, each of the one or more reporter layers comprising one or more concatemeric nucleic acid molecules and one or more reporter nucleic acid molecules for detection of the analyte,
   wherein immersion of the first end of the substrate in a solution comprising the analyte results in lateral flow of the solution from the first end of the substrate to the second end by capillary action and flow through the one or more reporter layers resulting in binding of the analyte with the concatemeric nucleic acid molecules, the binding detected by one or more reporter nucleic acid molecules for detection of the analyte.

5. The biosensor of claim 4, wherein the concatemeric nucleic acid molecules remain immobilized at their initial locations after flow of the analyte solution over the reporter layer.

6. The biosensor of claim 1, wherein the one or more reporter nucleic acid molecules for detection of the analyte comprise a detection system selected from a fluorescent system, a colorimetric system and an electrochemical system.

7. The biosensor of claim 6, wherein the one or more reporter nucleic acid molecules for detection of the analyte comprise a fluorescent system.

8. The biosensor of claim 1, wherein the printing is thermal ink-jet printing.

9. A method of detecting one or more analytes in a sample, wherein the sample is suspected of comprising the one or more analytes, the method comprising contacting the sample with the biosensor of claim 1 and monitoring the one or more reporter nucleic acid molecules for detection for a positive,
   wherein (a) when the one or more reporter nucleic acid molecules for detection comprises a fluorescent system, the positive result is a presence of a fluorescent signal on the biosensor, (b) when the one or more reporter nucleic acid molecules for detection comprises a colorimetric system, the positive result is a presence of a colorimetric signal on the biosensor or (c) when the one or more reporter nucleic acid molecules for detection comprises an electrochemical system, the positive result is a presence of an electrochemical signal on the biosensor, and wherein the positive result indicates the presence of the one or more analytes in the sample.

10. The method of claim 9, wherein the analyte is selected from metal ions, small molecule drugs, hormonal growth factors, biomolecules, toxins, peptides, proteins, viruses, bacterial, cells and tissues.

11. The method of claim 9, wherein the one or more reporter nucleic acid molecules for detection comprises a fluorescent system and the positive result is a presence of a fluorescent signal on the biosensor.

12. A kit comprising a biosensor of claim 1.

* * * * *

SEQUENCE LISTING

<160> NUMBER OF SEQ ID NOS: 14

<210> SEQ ID NO 1
<211> LENGTH: 63
<212> TYPE: DNA
<213> ORGANISM: Artificial Sequence
<220> FEATURE:
<223> OTHER INFORMATION: Synthetic

<400> SEQUENCE: 1

```
tgtcttcgcc tatagtgaac cttcctccgc aatactcccc caggtatctt tcgactaagc    60
acc                                                                  63

<210> SEQ ID NO 2
<211> LENGTH: 21
<212> TYPE: DNA
<213> ORGANISM: Artificial Sequence
<220> FEATURE:
<223> OTHER INFORMATION: Synthetic

<400> SEQUENCE: 2
ggcgaagaca ggtgcttagt c                                              21

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
gggggagtat tgcggaggaa                                                20

<210> SEQ ID NO 4
<211> LENGTH: 61
<212> TYPE: DNA
<213> ORGANISM: Artificial Sequence
<220> FEATURE:
<223> OTHER INFORMATION: Synthetic

<400> SEQUENCE: 4
tgcagcgact cacaggatca tggtgatgct ctacgtgccg tagcctgccc tttcgactac    60
c                                                                    61

<210> SEQ ID NO 5
<211> LENGTH: 21
<212> TYPE: DNA
<213> ORGANISM: Artificial Sequence
<220> FEATURE:
<223> OTHER INFORMATION: Synthetic

<400> SEQUENCE: 5
gagtcgctgc aggtagtcga a                                              21

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
cgtagagcat caccatgatc                                                20

<210> SEQ ID NO 7
<211> LENGTH: 16
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: fluorescein attached
```

```
<400> SEQUENCE: 7
cgactaagca cctgtc                                                16

<210> SEQ ID NO 8
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: dabcyl attached

<400> SEQUENCE: 8
cccaggtatc tt                                                    12

<210> SEQ ID NO 9
<211> LENGTH: 63
<212> TYPE: DNA
<213> ORGANISM: Artificial Sequence
<220> FEATURE:
<223> OTHER INFORMATION: Synthetic

<400> SEQUENCE: 9
tcactatagg cgaagacagg tgcttagtcg aaagatacct gggggagtat tgcggaggaa    60
ggt                                                              63

<210> SEQ ID NO 10
<211> LENGTH: 43
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (10)..(10)
<223> OTHER INFORMATION: fluorescein attached

<400> SEQUENCE: 10
tttttttttt tcactgacct gggggagtat tgcggaggaa ggt                  43

<210> SEQ ID NO 11
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: fluorescein attached

<400> SEQUENCE: 11
gactacctgc agcga                                                 15

<210> SEQ ID NO 12
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: dabcyl attached

<400> SEQUENCE: 12
```

```
agcctgccct tt                                                               12

<210> SEQ ID NO 13
<211> LENGTH: 61
<212> TYPE: DNA
<213> ORGANISM: Artificial Sequence
<220> FEATURE:
<223> OTHER INFORMATION: Synthetic

<400> SEQUENCE: 13
tgagtcgctg caggtagtcg aaagggcagg ctacggcacg tagagcatca ccatgatcct          60
g                                                                         61

<210> SEQ ID NO 14
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (12)..(12)
<223> OTHER INFORMATION: dabcyl attached

<400> SEQUENCE: 14
gggtccgtag ga                                                              12
```